United States Patent [19]

Moretti et al.

[11] Patent Number: 4,542,538

[45] Date of Patent: Sep. 24, 1985

[54] DISPOSABLE PROTECTIVE FILM ACCESSORY FOR THE LENS OF A RESPIRATOR HOOD

[75] Inventors: Anthony L. Moretti, San Rafael; Anselmo P. Pellolio, Jr., Cotati, both of Calif.

[73] Assignee: E. D. Bullard Company, Sausalito, Calif.

[21] Appl. No.: 680,145

[22] Filed: Dec. 10, 1984

Related U.S. Application Data

[63] Continuation-in-part of Ser. No. 574,015, Jan. 26, 1984, abandoned.

[51] Int. Cl.[4] .......... A61F 9/02; A42B 1/06

[52] U.S. Cl. .......... 2/438; 2/8; 2/205; 2/422

[58] Field of Search .......... 2/438, 422, 424, 435, 2/202, 205, 8, 9, 10

[56] References Cited

U.S. PATENT DOCUMENTS

| | | | |
|---|---|---|---|
| 1,994,103 | 3/1935 | Huey | 2/8 |
| 4,428,081 | 1/1984 | Smith | 2/438 |
| 4,455,689 | 6/1984 | Boyer | 2/434 |

FOREIGN PATENT DOCUMENTS

| | | | |
|---|---|---|---|
| 2511243 | 9/1976 | Fed. Rep. of Germany | 2/438 |
| 2819555 | 11/1979 | Fed. Rep. of Germany | 2/8 |

*Primary Examiner*—Werner H. Schroeder
*Assistant Examiner*—J. L. Kravitz
*Attorney, Agent, or Firm*—Robert W. Dilts

[57] ABSTRACT

A disposable protective film accessory for use with a hood assembly including an optically transparent lens panel. The accessory includes an elongated sheet of thin, flexible transparent film having a length many times the length of the lens panel and a width which is at least a substantial portion of the width of the lens panel. The sheet of film is tightly rolled about an axis normal to the length thereof. The roll of film is loosely contained in a housing comprising an open sided cavity which is mounted on the exterior surface of the lens panel at one end thereof with the open side of the cavity against the lens panel. A tensioning bar member is mounted across the other end of the lens panel in contact with the exterior surface thereof. The free end of the protective film is pulled out of the cavity between the housing and the lens panel, across the exterior surface of the lens panel and between the lens panel and the tensioning bar member. The edge of the sheet of protective film projecting beyond the tensioning bar member is slit to promote the tearing of the free end of the sheet of protective film by a twisting movement thereof against the tensioning bar member to enable the removal of contaminated portion of the film for disposal.

20 Claims, 12 Drawing Figures

FIG _ 4
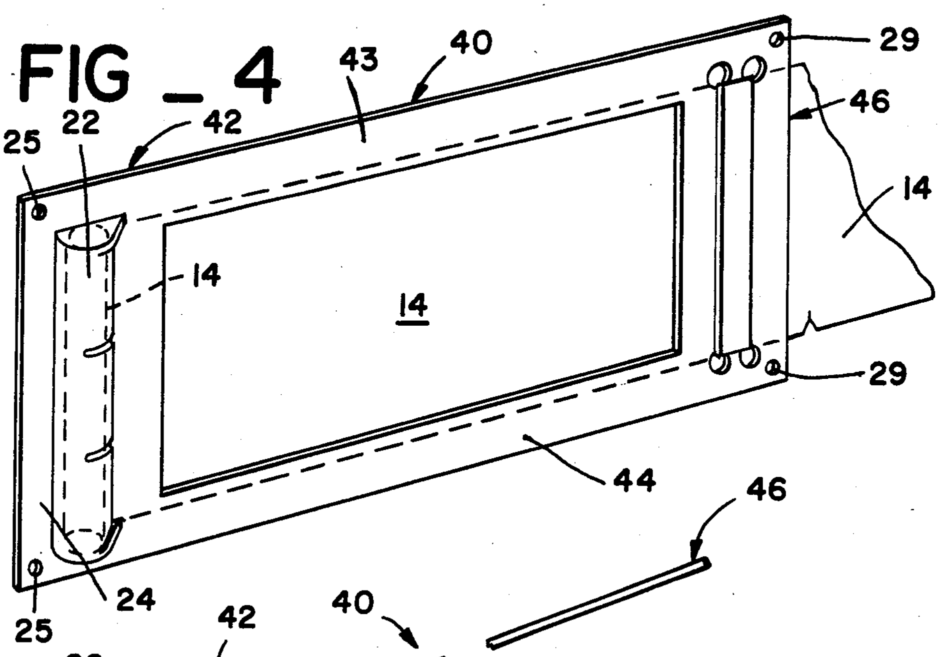
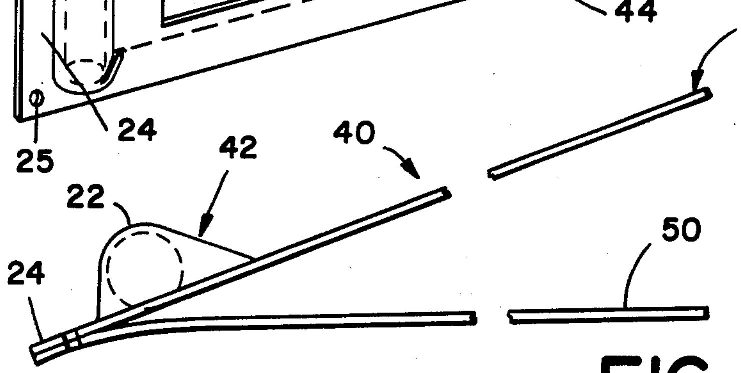
FIG _ 5
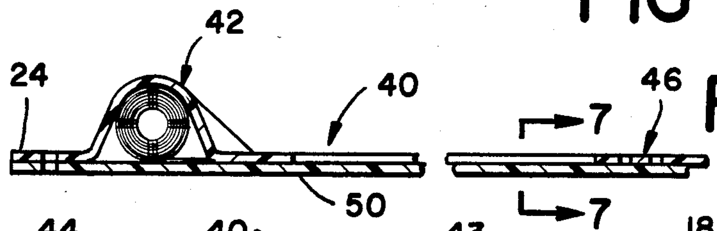
FIG _ 6
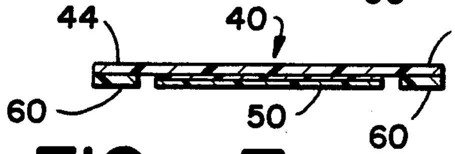
FIG _ 7
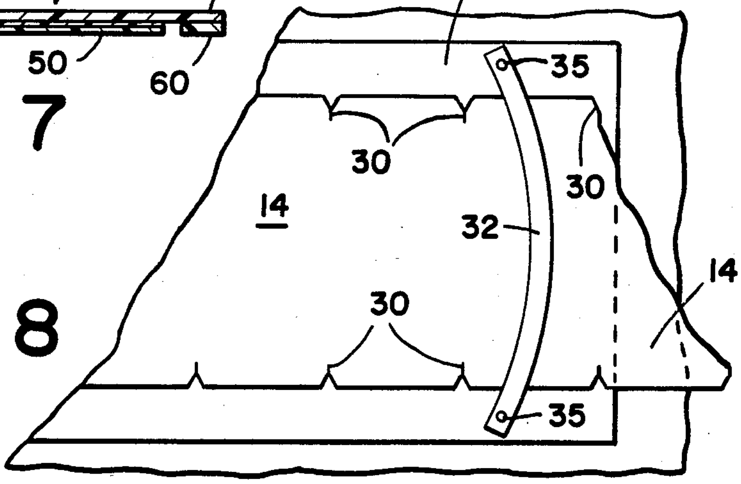
FIG _ 8

FIG_9
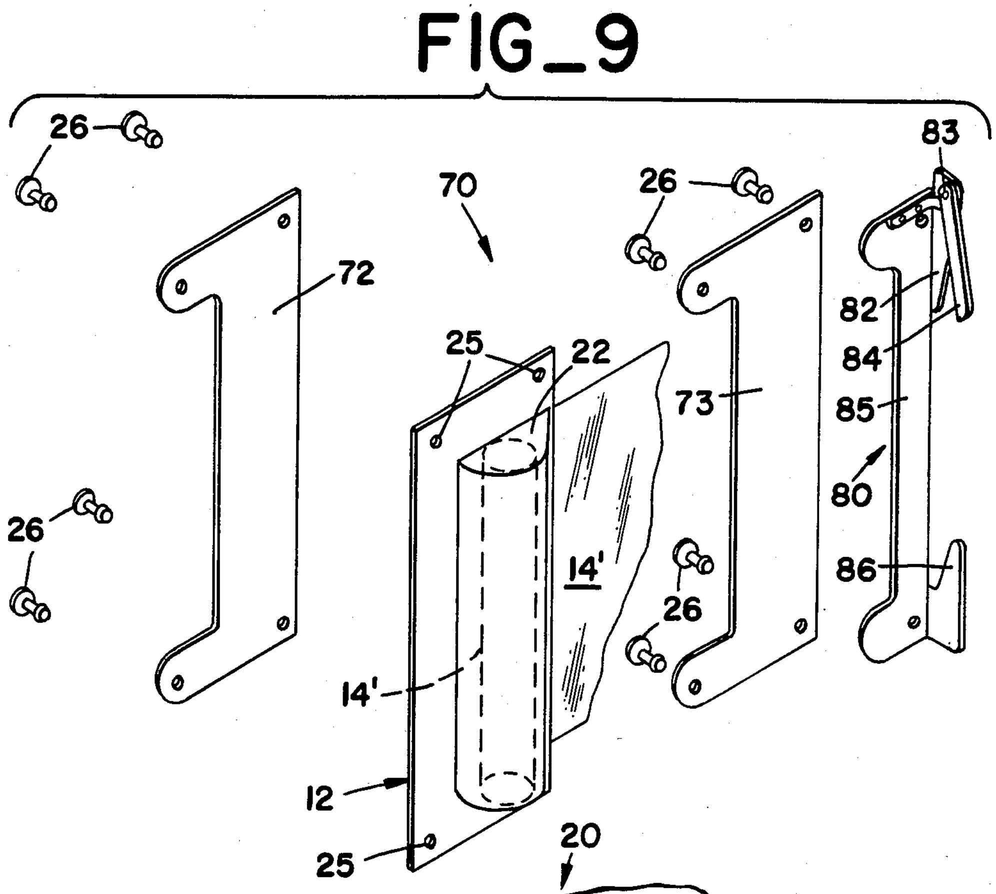
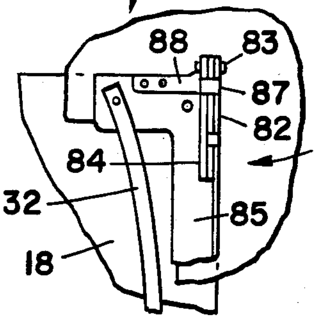
FIG_12
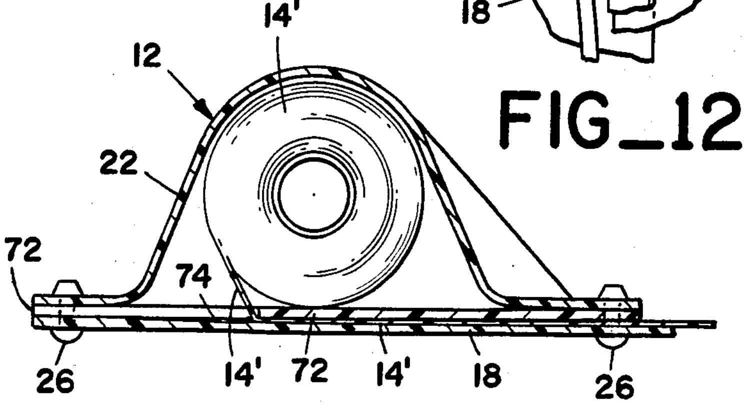
FIG_10
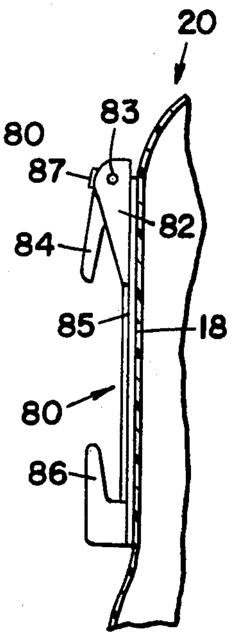
FIG_11

DISPOSABLE PROTECTIVE FILM ACCESSORY FOR THE LENS OF A RESPIRATOR HOOD

BACKGROUND OF THE INVENTION

Cross Reference to Related Application

This application is a continuation-in-part of applicants' prior application, Ser. No. 574,015, now abandoned, filed Jan. 26, 1984.

FIELD OF THE INVENTION

This invention relates to means for mounting a replaceable transparent protective film over the lens of a protective hood assembly and more particularly to an improved disposable film and film dispensing accessory.

Prior Art

Health and safety requirements dictate that those working in atmospheres contaminated with air-borne substances utilize an appropriate device for providing contaminant-free respiration air. In recent years, such devices have taken the form of a loose fitting supplied air respirator hood including a hollow, generally tubular body portion closed at one end made of flaccid non-stretchable air-impervious material and dimensioned to enclose the head and neck of the wearer. A curved, optically transparent lens panel is interposed in the side wall of the generally tubular body portion adjacent the closed end thereof to permit the wearer to visually monitor the work in progress. U.S. patent application Ser. No. 457,527 entitled "Loose Fitting Supplied Air Respirator Hood", filed Jan. 13, 1983 and assigned to the assignee of this application, discloses a disposable protective hood to which the invention of this application is particularly applicable.

Thus, it has been found that where a protective hood is used in painting or sandblasting, for example, the optically transparent lens panel will quickly become coated or pitted to an extent sufficient to seriously interfere with the ability of the wearer to visually observe the work in progress. It has been proposed in the prior art to employ means for mounting a replaceable protective film over the lens of the hood so that when the film has become pitted or covered with paint it may be removed and replaced with a new protective film. Thus, according to one approach taken in the prior art, arrangements for pay-out and removal of transparent film have been provided at opposite ends of the lens panel. However, such arrangements have included rigid housings including both a pay-out shaft and a take-up shaft with mechanisms for rotating at least the take-up shaft. Such arrangements have been expensive and complicated and are designed to be permanently mounted on non-disposable hoods.

It is the object of this invention to provide an accessory including a protective film and film dispensing means which is not only effective in protecting the lens panel of a respirator hood but which is simple and inexpensive enough to make it economically disposable.

SUMMARY OF THE INVENTION

A disposable protective film accessory according to this invention may be used with any face and head protective hood assembly having an optically transparent lens panel of a given length and a given width but is particularly suitable for use with a face and head protective hood assembly which is itself designed to be disposable. According to this invention, the accessory includes a sheet of thin, flexible protective film having a length many times greater than the given length of the lens panel and a width which is a substantial portion of the given width of the lens panel. The sheet of protective film is tightly rolled about an axis extending transversely of the length thereof. The tightly rolled sheet of film is loosely contained in a housing comprising an elongated open sided cavity having a depth greater than the diameter of the tightly rolled sheet and a length greater than the width of the sheet. The accessory also includes a tensioning bar member having a length greater than the given width of the sheet of protective film and means are provided for mounting the ends of the tensioning bar member to the lens with the portion of the bar member intermediate the ends thereof extending along one end of the lens in compressive unobstructed contact with the exterior surface of the lens. Means are also provided for mounting the ends of the housing to the lens with the open sided cavity in contact with the exterior surface of the lens panel and extending along the other end of the lens panel from the tensioning bar member. Thus the sides of the housing extend in spaced generally parallel relation to the tensioning bar member so that the sheet of protective film may be pulled out of the housing between the inner side of the housing and the exterior surface of the lens panel, across the exterior surface of the lens panel and between the tensioning bar member and the exterior surface of the lens panel to hold a length of the sheet of protective film in contact with the exterior surface of the lens panel. Slits provided in the film at the edge thereof promote the tearing of the free end of the sheet of protective film which projects beyond the tensioning bar by a manual twisting of the free end of the sheet of protective film against the tensioning bar for disposal of used portions of the protective sheet.

BRIEF DESCRIPTION OF THE DRAWING

This invention will be more fully understood from the following detailed description of preferred embodiments thereof when read in conjunction with the appended drawing wherein:

FIG. 4 is a perspective view of another embodiment of the disposable protective film dispensing accessory according to this invention.

FIG. 5 is a side view in elevation of a further embodiment of the disposable protective film dispensing accessory according to this invention shown in a partially disassembled state.

FIG. 6 is a side view in cross-section similar to FIG. 5 but showing the disposable protective film dispensing accessory immediately prior to mounting on the lens of a protective hood.

FIG. 7 is a cross-sectional view taken along line 7—7 of FIG. 6.

FIG. 8 is a fragmentary plan view similar to FIG. 3 but showing an alternate tensioning bar suitable for use in the embodiment of this invention as shown in FIG. 1.

FIG. 9 is an exploded perspective view of a further embodiment of the disposable protective film dispensing accessory according to this invention.

FIG. 10 is an enlarged cross-sectional view of the fully assembled housing of the embodiment of FIG. 9.

FIG. 11 is a reduced fragmentary end view partially in elevation and partially in cross-section showing the tensioning bar and slit cutter of the embodiment of FIG. 9 mounted on a hood assembly.

FIG. 12 is an enlarged fragmentary plan view of the slit cutter of the embodiment of FIG. 9.

DETAILED DESCRIPTION OF PREFERRED EMBODIMENTS

Figure 1:
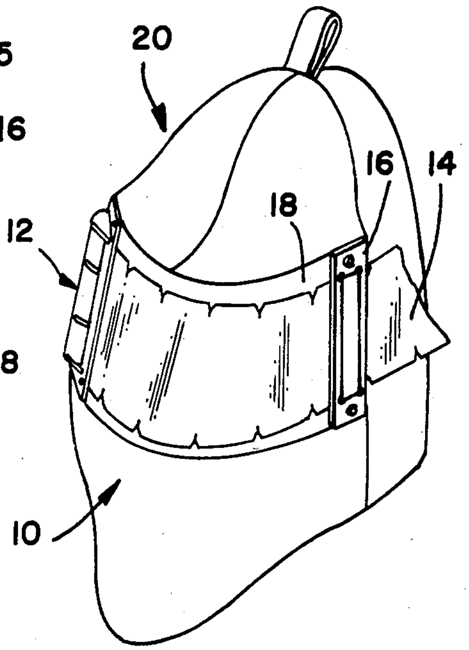
FIG. 1 is a perspective view of a disposable loose-fitting supplied air respirator hood having a disposable protective film dispensing accessory according to one embodiment of this invention mounted thereon.

Referring to FIG. 1, a disposable protective film dispensing accessory 10 comprising a housing 12 containing a roll of thin, flexible, protective film 14 and tensioning bar member 16 according to one embodiment of this invention is shown in perspective as mounted on the lens 18 of a loose fitting supplied air respirator hood assembly 20. According to the embodiment 10 of this invention, the housing 12 and tensioning bar member 16 are separate structural elements as best shown in FIG. 2.

As shown in FIG. 1, the lens 18 is a generally rectangular optically transparent panel interposed in the side wall of the hood assembly 20 having given length and width dimensions. The housing 12 is mounted along one end of the lens panel 18 and the tensioning bar member 16 is mounted along the other end of the lens panel 18.

The lens panel 18 must, of course, be sufficiently rigid to not only be self-supporting but to withstand the impact of air-borne particulate matter although the body of the hood assembly 20 may be essentially flaccid. The lens panel 18 may be curved along the length thereof to provide a convex exterior surface and a concave interior surface.

Figure 2:
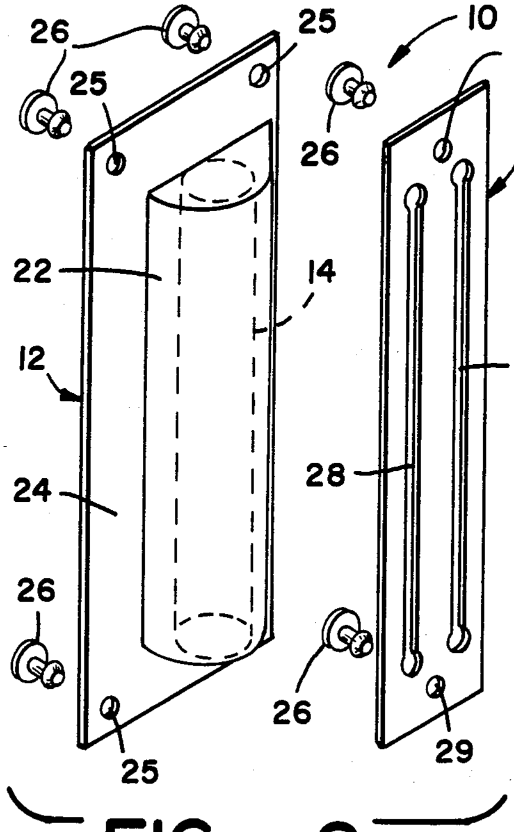
FIG. 2 is an exploded view of the essential elements of a disposable protective film dispensing accessory according to the embodiment of this invention shown in FIG. 1.

Referring to FIG. 2, the housing 12 and tensioning bar member 16 may comprise generally rectangular members of plastic sheet material, for example. The sheet material of which the housing 12 is made may be die formed or vacuum formed to provide an elongated cavity 22 extending longitudinally thereof and having a depth at least equal to the diameter of an unused roll of protective film 14. Thus a generally rectangular flange 24 will surround the open side of the cavity 22 and appropriate means may be provided for mounting the flange on the exterior surface of the lens 18 with the open side of the cavity 22 facing the lens and with the flange 24 in contact with the exterior surface of the lens 18. For example, double sided tape could be used along the ends and one side of the flange 24 leaving the other side of the flange unobstructed so that the protective film may pass between the unobstructed side of the flange 24 and the exterior surface of the lens 18.

However, as shown in FIG. 2, the flange 24 is provided with holes 25 at the four corners thereof and the housing 12 is mounted on the lens 18 by means of plastic pins 26 having a large head at one end and a beveled collar at the other end dimensioned to provide an interference fit with the holes 25. It will be understood that corresponding holes would be provided through the lens 18 to accommodate pins 26. The pins 26 will fill the holes through the lens 18 and flange 24 of the housing 12 with the large heads providing a sufficient seal for the supplied air respirator hood assembly 20. Thus the roll 14 of protective film will be captured in the cavity 22 against the exterior surface of the lens 18 and the free end thereof may pass between the exterior surface of the lens and the side of the flange 24 facing the center of the lens 18.

The tensioning bar member 16 may be provided with a pair of slots 28 extending longitudinally thereof in spaced parallel relation. The length of the slots 28 is slightly greater than the width of the protective film 14. A pair of holes 29 may be provided through the member 16 beyond the opposite ends of the slots 28 to enable the tensioning bar member 16 to be mounted on the exterior surface of the lens 18 by means of plastic pins 26 as described hereinabove in connection the the housing 12.

Figure 3:
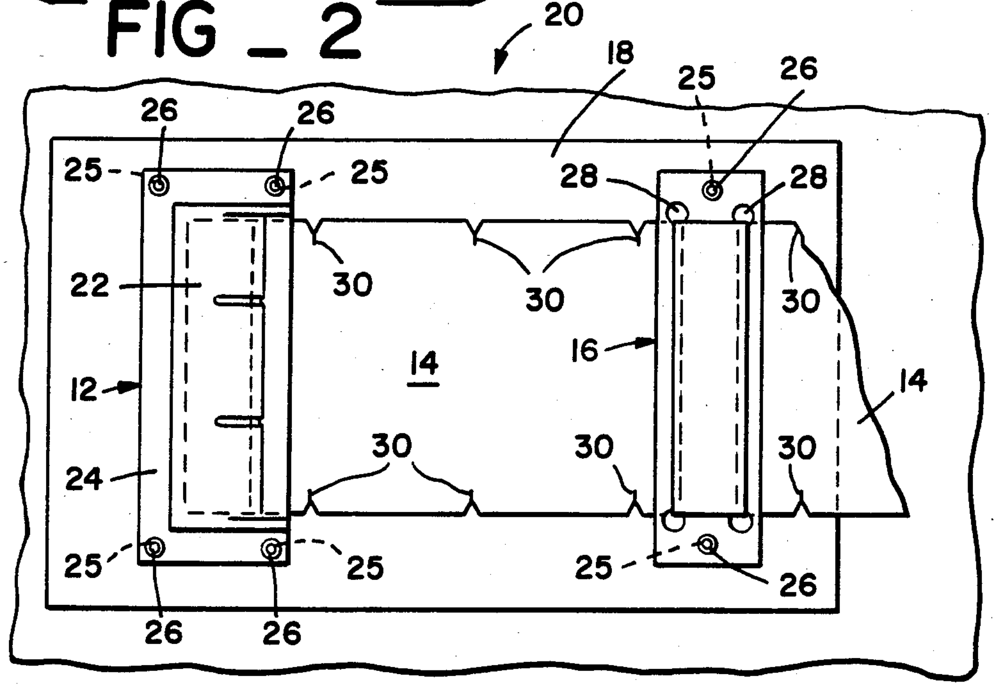
FIG. 3 is an enlarged plan view of the lens portion of the protective hood of FIG. 1 showing the disposable protective film dispensing accessory as mounted thereon.

Thus the film 14 may be pulled from the housing 12 across the exterior surface of the lens 18 and inserted under the tensioning member 16. The free end of the film 14 may then be passed outwardly through the first of the slots 28 to be encountered and reinserted back through the second of the slots 28 over the intervening portion of the tensioning member 16. As shown in FIGS. 1 and 3, the free end of the film 14 will project from beneath the tensioning member 16 so that it can be manually grasped by the hand of the wearer of the hood assembly 20.

As best shown in FIG. 3, the opposite edges of the film 14 are each provided with a plurality of slits 30 therein. The slits 30 on each edge of the film 14 are spaced from each other by a distance which is less than the spacing between the housing 12 and the tensioning member 16 and thus less than the length of the lens 18. The opposite edges of the film 14 may be notched at the slits 30 as shown in FIG. 3, if desired.

The purpose of the slits 30 is to promote the tearing of the film 14 by a twisting force exerted on the free end of the film 14 against the tensioning member 16 while exerting a slight longitudinal pull on the film 14. The resulting tear will provide a tail at the free end of the film 14 which can be subsequently grasped by the wearer of the hood assembly 20 to pull a new length of film 14 across the exterior surface of the lens 18 when the length of film previously covering the exterior surface of the lens 18 has been sufficiently coated with paint or pitted or otherwise contaminated in such a way as to obscure vision. The contaminated length of the film 14 may then be removed by tearing as described above.

Thus the length of the slits 30 along opposite edges of the film 14 must not exceed about 10% of the width of the film 14 in order to avoid unduly weakening the film 14 with respect to its ability to withstand forces required to pull it out of the housing across the exterior of the lens 18 and through the tensioning means 16. It should be pointed out that the tensioning means 16 does not contribute to the tearing off of the free end of the film 14 other than to provide the tension required to introduce forces at the slit 30 in the free end of the film 14 which is adjacent the tensioning means at the top edge of the film 14. The contaminated end torn off of the free end of the film 14 must, of course, be disposed of in an appropriate way, depending on the environment involved. To this end an appropriate pocket, bag or receptacle should be made available to the wearer of a hood assembly 20 equipped with an accessory 10 according to the teaching of this invention.

It has been found through experimental use that the free end of the protective film 14 will always tear in such a way as to provide a ragged portion projecting from under the tensioning member 16 due to the natural movement of the hand of a wearer of a protective hood assembly 20 provided with the accessory 10 according to the teaching of this invention. Thus the tension member 16 need not be rectilinear and need not have sharp edges. For example, referring to FIG. 8 of the drawing, embodiments of this invention have been made using a tensioning member 32 comprising a length of plastic tubing of small diameter sufficient to extend across the width of the lens 18 at one end thereof. The opposite ends of the tubing 32 may be provided with holes 35 to enable the tubing 32 to be mounted on the exterior surface of the lens 18 by means of pins 26 as described hereinabove in connection with the tensioning member 16.

The tubing 32 must lie in compressive contact with the exterior surface of the lens 18. However, it is not necessary that the tubing 32 be rectilinear. Instead, the axis of the tubing 32 is preferably curved along the surface of the lens 18 to provide a convex surface facing the free end of the film 14 and a concave surface facing the center of the lens 18, as shown in FIG. 8. The relationship between the holes 35 and the curvature of the tubing 32 will enable the compressive force between the tubing 32 and the exterior surface of the lens 18 to be increased. In addition, the convex curvature of the tubing 32 facing the free end of the film 14 will facilitate the tearing off of the free end of the film 14 by a twisting movement of the hand of the wearer as described hereinabove.

Referring to FIG. 4, another embodiment 40 of this invention is shown in which a housing 42 substantially identical to the housing 12 and a tensioning member 46 substantially identical to the tensioning member 16 are mechanically interconnected by upper and lower frame members 43 and 44. The roll of protective film 14 is identical to that described in connection with FIGS. 1–3. The frame members 43 and 44 are dimensioned to overlap the edges of the film 14 at the top and bottom respectively. As shown in FIG. 4, a pair of holes 25 are provided at the corners of the housing end of the embodiment 40 and a second pair of holes 29 are provided at the tensioning member end of the embodiment 40. Thus the embodiment 40 may be mounted on the exterior surface of a lens panel 18 by means of pins 26 passing through the holes 25 and 29 as described hereinabove.

The function of frame members 43 and 44 is to provide a unitary structure which may facilitate the mounting of the housing 42 and tensioning member 46 in certain applications. However, it has been found that the frame members 43 and 44 are unnecessary except under the most extreme environmental conditions.

Thus, referring to FIGS. 5 through 7, the embodiment 40 may be used with a backing plate 50 in order to meet extreme environmental conditions under which paint or particulate matter may tend to be forced between the film 14 and the exterior surface of the lens plate. As shown in FIG. 5, the backing plate 50 comprising a sheet of transparent material is fixed to the side of the flange 24 at the free side of the cavity 22 of the housing 42 and is otherwise free from attachment to the embodiment 40. Thus the embodiment 40 and the plate 50 may be spread as shown in FIG. 5 to enable the insertion of a roll of protective film 14 into the cavity 22 of the housing 42.

Referring to FIG. 6, it will be seen that the transparent backing plate 50 has a length sufficient to overlap both the open side of the cavity 42 and the tensioning member 46. Referring to FIG. 7, it will be seen that the transparent backing plate 50 has a width sufficient to overlap the inner edges only of the frame members 43 and 44. Thus the edges of the film 14 will be received between the backing plate 50 and the inner edges of the frame members 43 and 44. However, the outer portions of the frame members 43 and 44 will project beyond the plate member 50.

Where the embodiment 40 is combined with the backing plate 50 for use under severe environmental conditions, it is preferred to mount the structure on the lens 18 by means of double stick tape 60 as best shown in FIG. 7. Thus, a first strip of double stick tape 60 is interposed between the lens and the portion of the frame member 43 which projects beyond the backing plate 50. Similarly, a second strip of double stick tape 60 is interposed between the lens and the portion of the frame member 44 which projects beyond the backing plate member 50. Such double stick tape preferably extends the full length of the structure and thus covers the mounting holes 25 and 29 as well as the corresponding holes provided through the lens 18.

Where the backing plate 50 is used in conjunction with the embodiment 40 and the combined structure mounted with double stick tape 60 as described above, the entry of air-borne particulate matter between the lens and the film will be substantially eliminated. It is important that the end of the backing plate 50 which overlaps the tensioning member 46 be free of mechanical interconnection in order for the combined structure to accommodate any curvature that may be present in the lens to which the structure is mounted. If such end of the backing plate 50 is not free, then the bending of the structure to accommodate any curvature in the lens will tend to force the backing plate 50 into compressive contact with the frame members 43 and 44, trapping the film 14 therebetween and causing the film 14 to bind and tear in the structure.

Referring to FIG. 9, a further embodiment 70 of this invention is shown. The housing 12 and cavity 22 of the embodiment 70 is identical to that of the embodiment 10 shown in FIG. 1. However, according to the embodiment 70, a tensioning plate 72 is applied to the housing 12 to partially close the open-sided cavity 22. Thus the tensioning plate 72 is adapted to be sandwiched between the housing 12 and the exterior surface of the lens 18 of the hood assembly 20 at one end thereof. A similar tensioning plate 73 may be mounted along the exterior surface of the lens panel 18 at the other end thereof to provide a tensioning member equivalent to tensioning members 16 and 32 as described hereinabove.

As best shown in FIG. 10, the tensioning plate 72 is dimensioned to cover all but a narrow slot 74 extending along one side of the cavity 22. The slot 74 is dimensioned to pass the free end of the protective film 14' from a roll retained in the cavity 22 by the tensioning plate 72.

Thus the housing 12 and tensioning plate 72 are assembled and mounted to the lens 18 with the slot 74 extending along the opposite side of the cavity 22 from the tensioning plate 73 and with the protective film 14' projecting through the slot and sandwiched between the lens 18 and the tensioning plate 72. The frictional forces resulting from the sandwiching of the protective film 14' between the exterior surface of the lens 18 and the tensioning plate 72 closing the bottom of the cavity 22 will help to insure that the protective film 14′ is maintained in contact with the exterior surface of the lens 18 during its travel between the housing 12 and the tensioning member 73. The protective film 14′ will, of course, also pass between the exterior surface of the lens 18 and the tensioning plate 73 at the opposite end of the lens 18 from the housing 12.

According to the embodiment 70 shown in FIG. 9, the roll of protective film 14′ differs from the roll of protective film 14 of the embodiment 10 and 40 in that no slits are provided in either edge of the protective film 14′. Instead a slitting device 80 is provided on the opposite side of the tensioning member 73 from the housing 12, as shown in FIGS. 9, 11 and 12.

As best shown in FIGS. 9 and 11, the slitting device 80 may comprise a knife means in the form of a pair of blades 82 and 84 interconnected with each other at one end by means of a pivot pin 83 to provide a scissors type action. One of the blades 82 is fixed along one end of a mounting strip 85 with the other of the blades 84 pivoted about the pin 83 to enable it to project at an angle from the mounting plate.

As best shown in FIG. 11, the mounting strip 85 is mounted to the lens 18 of the hood structure 20 together with the tension member 73 so that the top edge of the protective film 14′ will be received between the blades 82 and 84. As shown in FIGS. 9 and 11, the bottom edge of the protective film 14′ is received in a notch provided by L-shaped guide member 86 mounted on the opposite end of the mounting strip 85 from the blades 82 and 84.

As best shown in FIGS. 11 and 12, a stop means 87 is provided to limit the rotation of the blade 84 about the pivot pin 83 away from the mounting strip 85. In addition, the blade 84 is spring-loaded to urge it into engagement with the stop means 87. For example, as shown in FIG. 12, a leaf spring 88 of the cantilever type may be positioned to engage the blade 84 adjacent the pivot pin 83 to urge the blade 84 into engagement with the stop means 87.

As shown in FIG. 9, the blades 82 and 84 must be positioned on the opposite side of the tensioning bar member 73 from the housing 12. Thus, as shown in FIG. 12, a tensioning bar member 32 as described in connection with FIG. 8 may be used in place of and is preferred over tensioning plate 73 or tensioning bar member 16 and 26 for use in connection with the slitting means 80 as described hereinabove.

In operation, the free end of the protective film 14′ projecting from beneath the tensioning bar member 16, 26, 32, 73 would be received between the blades 82 and 84 and in the notch provided by the guide member 86 with the upper edge of the protective film being received between the blades 82 and 84 and the lower edge of the film 14′ received in the notch provided by the guide member 86. When the portion of the protective film 14′ covering the face plate 18 has become soiled in use, the free end of the film 14′ will be pulled until the soiled portion of the film 14′ projects on the opposite side of the slitting means 80 from the tensioning bar member. The user will then manually rotate the blade 84 about the pivot pin toward the blade 82 against the force of the leaf spring 88 making a short slit in the upper edge of the film 14′ therebetween. The free end of the film 14′ may then be torn off as described hereinabove for disposal. The natural tearing action of the film 14′ will tend to leave an attached end portion in engagement with the guide means 86 which may be easily grasped by the hand of the user in order to remove a further soiled portion of the film 14′ in the future as desired.

The embodiments of this invention as specifically described hereinabove have been reduced to practice with a loose fitting supplied air respirator hood 20 having a curved optical lens panel 18 with a length of about twelve inches (30 cm) and a width of about six inches (15 cm). The protective film 14, 14′ used had a length of about twenty times the length of the lens panel 18 and a width of about four and three-quarter inches (12 cm). Film made of mylar was used but acetate film could also be used. Film thickness between one-half mil and six mils were found to be satisfactory. The film was purchased from the manufacturer in large quantity supply rolls and both edges of the film may be slit and notched while still in the large quantity supply rolls. The film was subsequently removed from the large quantity supply rolls in a plurality of rolls of the above-mentioned length having a diameter of about three-quarters inch (2 cm).

The housings 12 (42) and tension members 16 (46) were made of rectangular polyester sheets 0.02 inch (0.05 cm) thick and about six inches (16 cm) long. The housings 12 (42) were about two and one-half inches (6 cm) wide including the flanges and were vacuum formed to provide cavities about one inch (2.5 cm) in depth. The tension members were about one inch (2.5 cm) wide and were provided with symmetrically arranged parallel slots about five inches (13 cm) long including stress relief holes at the opposite ends thereof.

The slits in the edges of the film 14 were about one-quarter inch (0.5 cm) long transversely of the length of the film. The slits were perpendicular to the edges of the film and were provided at both edges of the film so that the housing and tensioning member could be mounted for either right-handed or left-handed use. In other words, the housing may be mounted at either end of the lens with the tensioning member at the opposite end therefrom and with the upper edge of the film in either orientation being slit to facilitate the tearing off of the free end of the film as described hereinabove.

It is believed that those skilled in the art will make obvious modifications in and combinations of the embodiments of this invention as disclosed hereinabove without departing from the scope of the following claims. For example, changes in the materials and dimensions of the embodiments of this invention as specifically described above may be made as desired or a tensioning plate 72 may be sandwiched between the housing 42 of the embodiment 40 and the lens 18 or backing plate 50, if desired. Similarly, in embodiment 10, the tensioning plate 72 may be made as an integral and bendable flap or extension of a side or end of the cavity 22 of the housing 12 replacing a corresponding portion of the flange 24. In fact, the entire flange 24 may be replaced by a pair of integral and bendable flaps or extensions of opposite sides or ends of the cavity 22, one of which is dimensioned to serve as a tensioning plate 72 and the other of which captures the film 14 against the tensioning plate 72 and serves as a mounting plate which may be fixed to the lens 18 by double stick tape, for example, to mount the housing 12.

What is claimed is:

1. A disposable protective film accessory for use with a face and head protective hood assembly including an optically transparent lens panel of a given length and a given width, said accessory comprising:

(a) an elongated sheet of thin, flexible transparent protective film having a length many times greater than said given length of said lens panel and a width which is at least a substantial portion of said given width of said lens panel, a longitudinal side of said sheet of protective film having a plurality of short slits therein extending transversely of the length of said sheet and spaced from each other by a distance less than said given length of said lens panel, said sheet of protective film being rolled about an axis extending normally to the length thereof;

(b) a housing loosely containing said rolled sheet of protective film, said housing comprising an elongated open sided cavity having a depth greater than the diameter of said rolled sheet of protective film and a length greater than said given width of said sheet of protective film, said housing including a flat rectangular flange surrounding said open sided cavity;

(c) a tensioning bar member having a length greater than said given width of said sheet of protective film;

(d) means for mounting the ends of said tensioning bar to said lens panel with the portion of said tensioning bar member intermediate the ends thereof extending along one end of said lens panel in compressive unobstructed contact with the exterior surface of said lens panel, and (e) means for mounting the ends of said rectangular flange of said housing in compressive contact with the exterior surface of said lens panel with one side of said rectangular flange extending along the other end of said lens panel and with the other side of said rectangular flange in spaced generally parallel relation to said tensioning bar member and in compressive unobstructed contact with the exterior surface of said lens panel;

whereby the free end of said sheet of protective film may be pulled out of said housing between said other side of said flange and the exterior surface of said lens panel, across said exterior surface of said lens panel and between said tensioning bar member and said exterior surface of said lens panel to hold a length of said sheet of protective film in contact with said exterior surface of said lens panel and whereby said slits promote the tearing of the free end of said sheet of protective film projecting beyond said tensioning bar by a manual twisting of said free end of said sheet of protective film against said tensioning bar member.

2. A disposable protective film accessory as claimed in claim 1 wherein each of the longitudinal sides of said sheet of protective film is provided with a plurality of short slits therein spaced from each other by a distance less than said given length of said lens panel.

3. A disposable protective film accessory as claimed in claim 1 wherein said longitudinal side of said sheet of protective film is notched at each of said plurality of short slits therein.

4. A disposable protective film accessory as claimed in claim 1 wherein said housing comprises a thin walled semi-rigid body of synthetic material having said cavity formed centrally thereof with the remainder of said body providing said flat rectangular flange surrounding said cavity.

5. A disposable protective film accessory as claimed in claim 4 wherein said tensioning bar member comprises a thin flat sheet of synthetic material having a pair of longitudinally extending parallel slots therein, said slots having a length greater than the width of said sheet of protective film.

6. A disposable protective film accessory as claimed in claim 5 wherein said synthetic material is selected from the group consisting of polyester, acetate and polycarbonate, and wherein said sheet of film is made of a material selected from the group consisting of mylar and acetate.

7. A disposable protective film accessory as claimed in claim 6 wherein said housing and said tensioning bar member are interconnected at opposite ends thereof by a pair of generally parallel elongated frame members made of said synthetic material.

8. A disposable protective film accessory as claimed in claim 7 wherein said housing, said tensioning bar member and said frame members define a rectangular opening having a width less than said width of said sheet of protective film.

9. A disposable protective film accessory as claimed in claim 8 wherein a thin, flat, semi-rigid rectangular panel of transparent synthetic material having a width about equal to said width of said sheet of protective film and a length about equal to said length of said lens panel is rigidly mounted along one of its ends to the free side of said rectangular flange of said housing, said semi-rigid panel of transparent synthetic material being otherwise free of attachment to said housing, said frame members and said tensioning bar member.

10. A disposable protective film accessory as claimed in claim 1 wherein a thin, flat panel member dimensioned to close the open side of said cavity of said housing is rigidly fixed to both ends and one side of said flat rectangular flange surrounding said open sided cavity.

11. A disposable protective film accessory as claimed in claim 1 wherein said tensioning bar member comprises a cylindrical body of small diameter.

12. A disposable protective film accessory as claimed in claim 11 wherein said cylindrical body is curved in one dimension along the length thereof and mounted on said lens panel to present the concave side thereof to said housing and the convex side thereof to said free end of said sheet of protective film.

13. A disposable protective film accessory as claimed in claim 12 wherein said cylindrical body is an arcuate length of plastic tubing of small diameter.

14. A disposable protective film accessory as claimed in claim 1 wherein said lens panel has a pair of small diameter holes therethrough at each end thereof, each pair of small diameter holes being spaced from each other by a distance greater than said width of said sheet of protective film; the ends of said rectangular flange of said housing each have a different one of a pair of small diameter holes therethrough which are positioned to be brought into registry with said pair of holes at one end of said lens panel; the ends of said tensioning bar member each having a different one of a pair of small diameter holes therethrough which are positioned to be brought into registry with said pair of holes at the other end of said lens panel, said means for mounting the ends of said tensioning bar member to said lens panel comprises a first pair of pins each having a head at one end of larger diameter than said small diameter holes and a tapered collar at the other end dimensioned to provide an interference fit with said small diameter holes; and said means for mounting the ends of said rectangular flange of said housing comprises a second pair of pins each having a head at one end of larger diameter than said small diameter holes and a tapered collar at the other end dimensioned to provide an interference fit with said small diameter holes.

15. A disposable protective film accessory as claimed in claim 9 wherein said means for mounting the ends of said tensioning bar member to said lens panel and said means for mounting the ends of said rectangular flange of said housing to said lens panel are provided by a pair of elongated strips of double stick tape each extending along a different one of said pair of frame members and overlapping the associated ends of said rectangular flange of said housing and said tensioning bar member.

16. A disposable protective film accessory for use with a face protective assembly including an optically transparent lens panel of a given length and a given width, said accessory comprising:

(a) an elongated sheet of thin, flexible transparent protective film having a length many times greater than said given length of said lens panel and a width which is at least a substantial portion of said given width of said lens panel, said sheet of protective film being rolled about an axis extending normally to the length thereof;

(b) a housing loosely containing said rolled sheet of protective film, said housing comprising an elongated open cavity having a depth greater than the diameter of said rolled sheet of protective film and a length greater than said given width of said sheet of protective film;

(c) a tensioning bar member having a length greater than said given width of said sheet of protective film;

(d) means for mounting the ends of said tensioning bar member to said lens panel with the portion of said tensioning bar member intermediate the ends thereof extending along one end of said lens panel in unobstructed relation to the exterior surface of said lens panel;

(e) means for mounting said housing on the exterior surface of said lens panel with one side of said elongated open cavity extending along the other end of said lens panel and with the other side of said elongated open cavity in spaced generally parallel relation to said tensioning bar member and in unobstructed relation to said exterior surface of said lens panel; whereby the free end of said sheet of protective film may be pulled out of said housing between said other side of said housing and said exterior surface of said lens panel, across said exterior surface of said lens panel and between said tensioning bar member and said exterior surface of said lens panel to hold a length of said sheet of protective film in contact with said exterior surface of said lens panel and;

(f) a short slit in the edge of said free end of said sheet of protective film on the opposite side of said tensioning bar member from said housing whereby said free end of said sheet of protective film projecting beyond said tensioning bar member may be torn off by manual twisting of said free end of said sheet of protective film against said tensioning bar member.

17. A disposable protective film accessory as claimed in claim 16 wherein the edge of said sheet of protective film is provided with a plurality of short slits therein spaced from each other by a distance less than said given length of said lens panel.

18. A disposable protective film accessory as claimed in claim 16 wherein means for making a short slit in the edge of said sheet of protective film is provided on the opposite side of said tensioning bar member from said housing.

19. A disposable protective film accessory for use with a face protective assembly as claimed in claim 16 including a tensioning plate partially closing said elongated open cavity of said housing to provide a slot along said one side thereof dimensioned to pass said sheet of protective film, whereby said film may be pulled out of said housing through said slot and between said tensioning plate and said exterior surface of said lens panel.

20. A disposable protective film accessory for use with a face protective assembly as claimed in claim 18 wherein said means for making a short slit in the edge of said sheet of protective film comprises a knife means mounted on the opposite side of said tensioning bar member from said housing.

* * * * *